US012636202B2

(12) United States Patent
Chong et al.

(10) Patent No.: US 12,636,202 B2
(45) Date of Patent: May 26, 2026

(54) QUICK DRYING MOISTURE MANAGEMENT PANT

(71) Applicant: MODIBODI AUSTRALIA PTY LTD, New South Wales (AU)

(72) Inventors: Kristy Chong, New South Wales (AU); Alice Warner, New South Wales (AU)

(73) Assignee: MODIBODI AUSTRALIA PTY LTD, New South Wales (AU)

( * ) Notice: Subject to any disclaimer, the term of this patent is extended or adjusted under 35 U.S.C. 154(b) by 327 days.

(21) Appl. No.: 18/560,985

(22) PCT Filed: Apr. 14, 2022

(86) PCT No.: PCT/AU2022/050346
§ 371 (c)(1),
(2) Date: Nov. 15, 2023

(87) PCT Pub. No.: WO2022/246495
PCT Pub. Date: Dec. 1, 2022

(65) Prior Publication Data
US 2024/0269013 A1 Aug. 15, 2024

(30) Foreign Application Priority Data

May 27, 2021 (AU) ................................ 2021901589
May 27, 2021 (AU) ................................ 2021901597

(51) Int. Cl.
*A61F 13/496* (2006.01)
*A61F 13/15* (2006.01)
(Continued)

(52) U.S. Cl.
CPC ...... *A61F 13/496* (2013.01); *A61F 13/15203* (2013.01); *A61F 13/505* (2013.01); (Continued)

(58) Field of Classification Search
CPC .............. A61F 13/505; A61F 13/49006; A61F 13/496; A61F 13/74; A61F 13/49004; (Continued)

(56) References Cited

U.S. PATENT DOCUMENTS 4,968,312 A * 11/1990 Khan .................... A61F 13/551
604/385.13
4,981,480 A 1/1991 Gaudet et al.
(Continued)

FOREIGN PATENT DOCUMENTS

CA 2255465 A1 6/2000
EP 0274752 A2 7/1988
(Continued)

OTHER PUBLICATIONS

International Search Report (PCT/ISA/210) and Written Opinion (PCT/ISA/237) mailed on Jun. 3, 2022, by the Australian Patent Office as the International Searching Authority for International Application No. PCT/AU2022/050346.
(Continued)

*Primary Examiner* — Adam Marcetich
(74) *Attorney, Agent, or Firm* — BUCHANAN INGERSOLL & ROONEY PC

(57) ABSTRACT

A moisture management pant undergarment for wicking bodily fluid away from a wearer's skin into a fluid trapping core component of the undergarment, the garment comprising a pant body having leg openings having a crotch panel disposed therebetween, wherein at least a portion of the crotch panel is overlaid with a floating liner assembly partially fixedly attached to the pant body and adapted to accommodate the fluid trapping core component which traps bodily fluid wicked away from the wearer's skin, wherein at least one or more portions of the floating liner assembly and
(Continued)

the crotch panel can be physically separated from each other to expose the fluid trapping core component to aid drying.

19 Claims, 5 Drawing Sheets

(51) Int. Cl.

| | |
|---|---|
| *A61F 13/505* | (2006.01) |
| *A61F 13/56* | (2006.01) |
| *A61F 13/62* | (2006.01) |
| *A61F 13/70* | (2006.01) |
| *A61F 13/74* | (2006.01) |

(52) U.S. Cl.
CPC .......... *A61F 13/5638* (2013.01); *A61F 13/62* (2013.01); *A61F 13/70* (2013.01); *A61F 13/74* (2013.01); *A61F 2013/15487* (2013.01)

(58) Field of Classification Search
CPC .... A61F 13/15268; A61F 13/70; A61F 13/72; A61F 13/4906; A61F 2013/5055; A61F 13/49003; A61F 13/5638; A61F 13/84; A61F 13/49058
See application file for complete search history.

(56) References Cited

U.S. PATENT DOCUMENTS

| | | | | |
|---|---|---|---|---|
| 5,325,543 | A | 7/1994 | Allen | |
| 5,562,648 | A | 10/1996 | Peterson | |
| 5,669,902 | A | 9/1997 | Sivilich | |
| 5,707,364 | A | 1/1998 | Coates | |
| 6,423,047 | B1 * | 7/2002 | Webster ................ | A61F 13/505 |
| | | | | 604/397 |
| 2005/0131382 | A1 * | 6/2005 | Brud ....................... | A61F 13/66 |
| | | | | 604/401 |
| 2005/0256491 | A1 | 11/2005 | Watanabe et al. | |
| 2008/0015538 | A1 | 1/2008 | Deerin | |
| 2009/0299313 | A1 | 12/2009 | Knightingale et al. | |
| 2011/0319852 | A1 * | 12/2011 | Labit ..................... | A61F 13/493 |
| | | | | 604/385.01 |
| 2012/0116340 | A1 * | 5/2012 | Labit ................. | A61F 13/15268 |
| | | | | 604/377 |
| 2013/0006210 | A1 * | 1/2013 | Coates ............. | A61F 13/15268 |
| | | | | 604/385.14 |
| 2013/0012903 | A1 * | 1/2013 | Labit ..................... | A61F 13/493 |
| | | | | 604/378 |
| 2013/0133121 | A1 | 5/2013 | Parker | |
| 2013/0237940 | A1 * | 9/2013 | Wang ................ | A61F 13/49004 |
| | | | | 604/377 |
| 2014/0005621 | A1 | 1/2014 | Roe et al. | |
| 2014/0018763 | A1 | 1/2014 | Evenson et al. | |
| 2015/0065979 | A1 * | 3/2015 | Coates .................. | A61F 13/622 |
| | | | | 604/377 |
| 2019/0320727 | A1 * | 10/2019 | Bain ........................ | A41B 9/12 |
| 2021/0100698 | A1 | 4/2021 | Langdon et al. | |
| 2021/0352970 | A1 * | 11/2021 | Monaco ................. | A41B 9/007 |
| 2022/0096280 | A1 * | 3/2022 | Medvedev ........ | A61F 13/15268 |
| 2022/0160552 | A1 * | 5/2022 | Carpenter ............ | A61F 13/537 |
| 2023/0181388 | A1 * | 6/2023 | Smith ..................... | A61F 13/45 |
| | | | | 604/358 |

FOREIGN PATENT DOCUMENTS

| | | | | |
|---|---|---|---|---|
| EP | 0811362 | A1 | 12/1997 | |
| EP | 0696910 | B1 * | 11/2000 | ........ A61F 13/5638 |
| EP | 1166738 | A2 | 1/2002 | |
| EP | 2255761 | A1 | 12/2010 | |
| GB | 2144995 | A | 3/1985 | |
| GB | 2452052 | A | 2/2009 | |
| JP | H10121301 | A | 5/1998 | |
| JP | 2010233602 | A | 10/2010 | |
| JP | 2018075313 | A | 5/2018 | |
| JP | 2021070894 | A | 5/2021 | |
| JP | 2022114484 | A * | 8/2022 | .......... A61F 13/505 |
| KR | 1020200005031 | | 1/2020 | |
| WO | 9965438 | A1 | 12/1999 | |
| WO | 2010111717 | A1 | 9/2010 | |
| WO | 2017152222 | A1 | 9/2017 | |
| WO | WO-2020090189 | A1 * | 5/2020 | ............... A41B 9/04 |

OTHER PUBLICATIONS

Office Action (Examination Report No. 2) issued on Jul. 18, 2025, by the Australian Patent Office in corresponding Australian Patent Application No. 2022280533. (4 pages).

Office Action (Examination Report No. 1) issued on May 8, 2025, by the Australian Patent Office in corresponding Australian Patent Application No. 2022280533. (6 pages).

The extended European Search Report issued on May 15, 2025, by the European Patent Office in corresponding European Application No. 22809950.3. (8 pages).

* cited by examiner

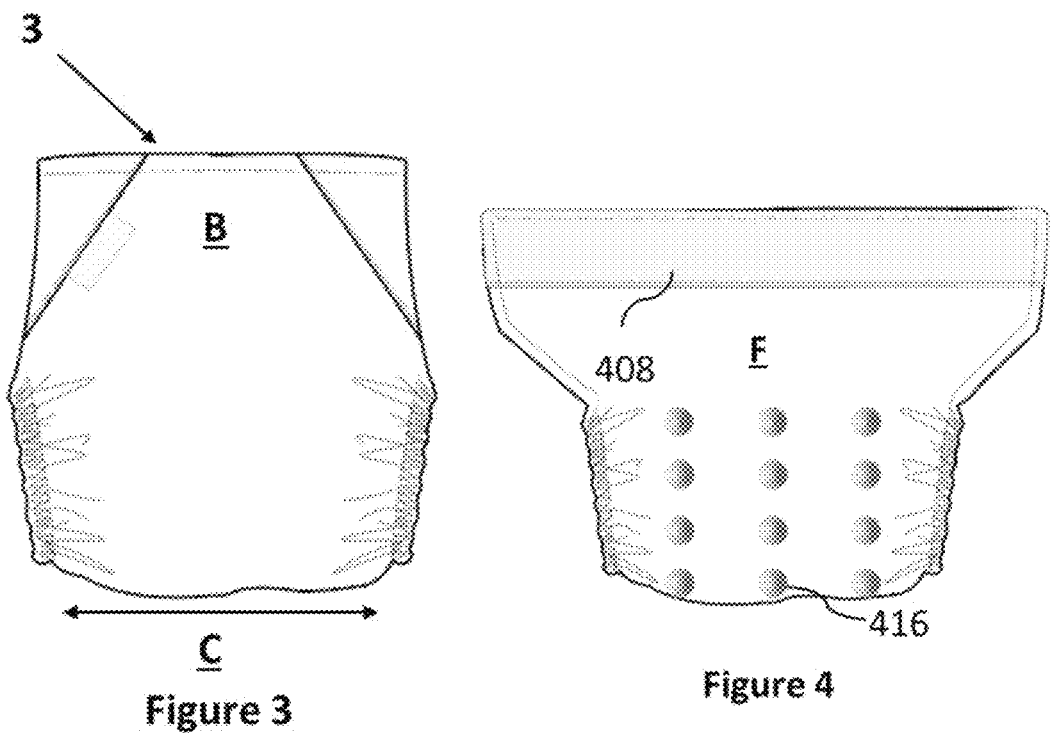
Figure 3
Figure 4
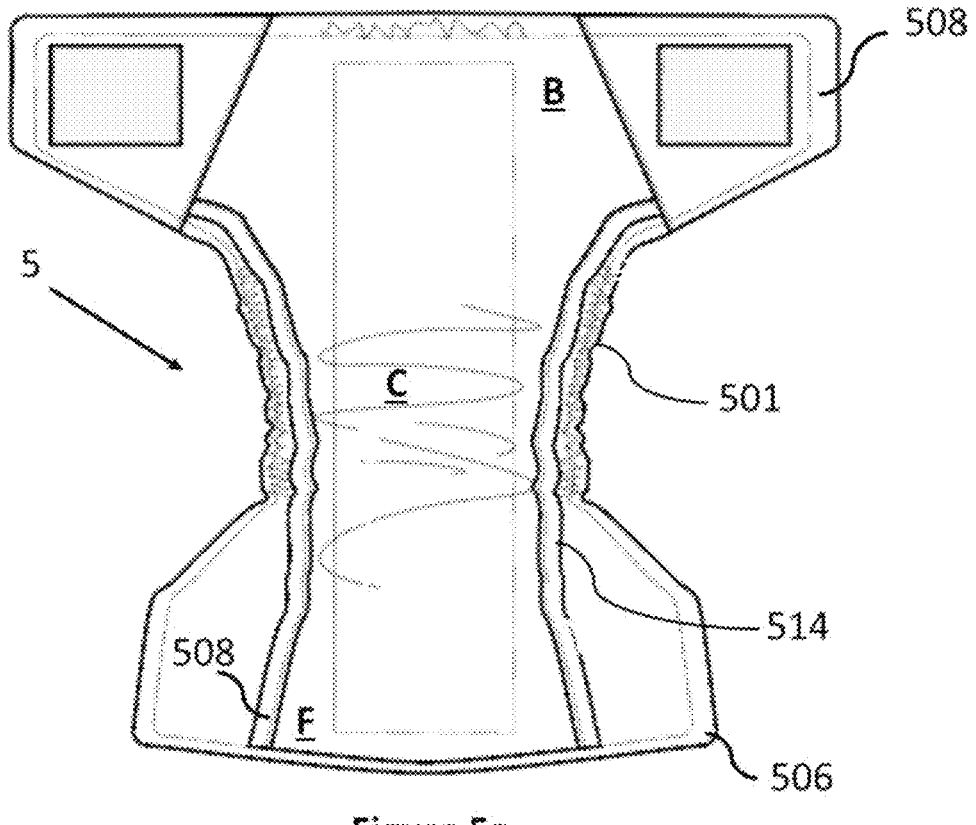
Figure 5a

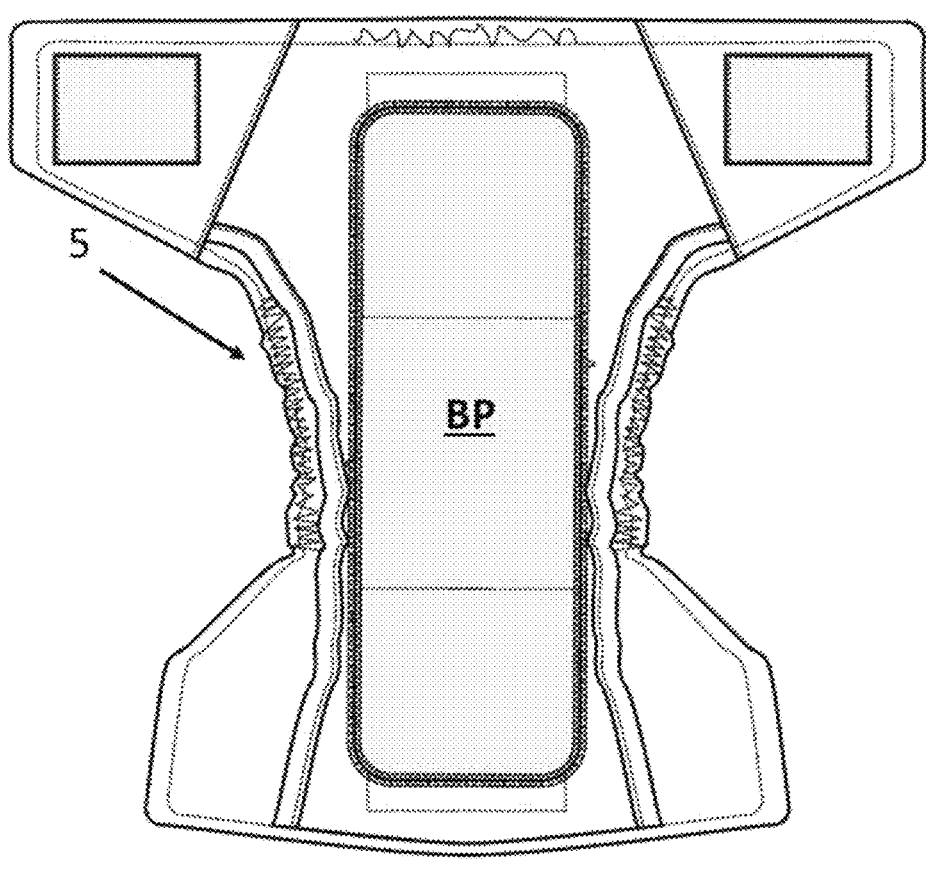
Figure 5b
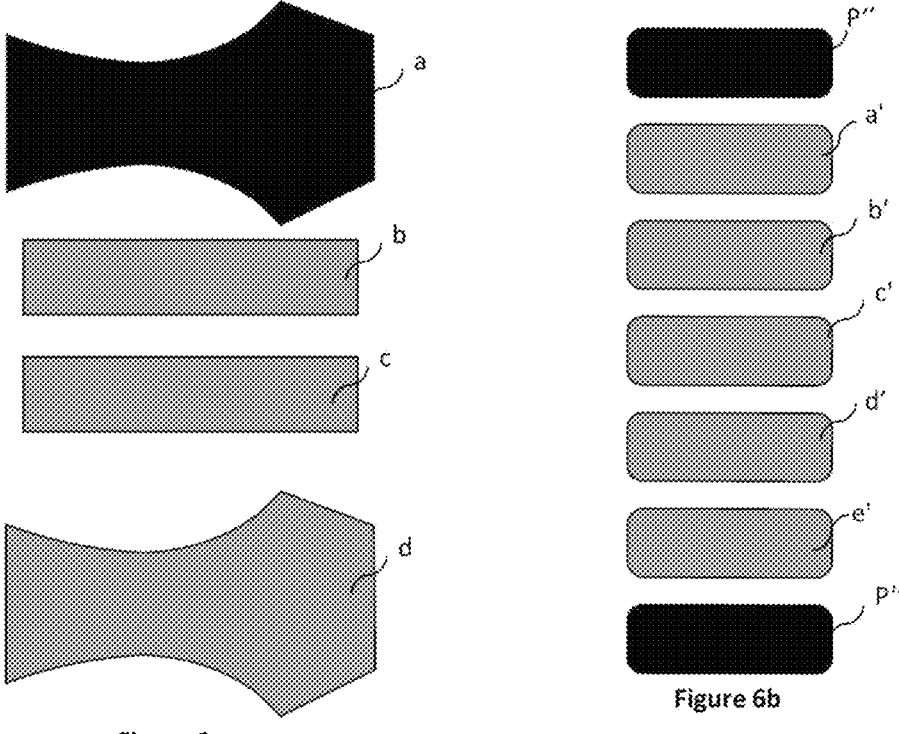
Figure 6a
Figure 6b

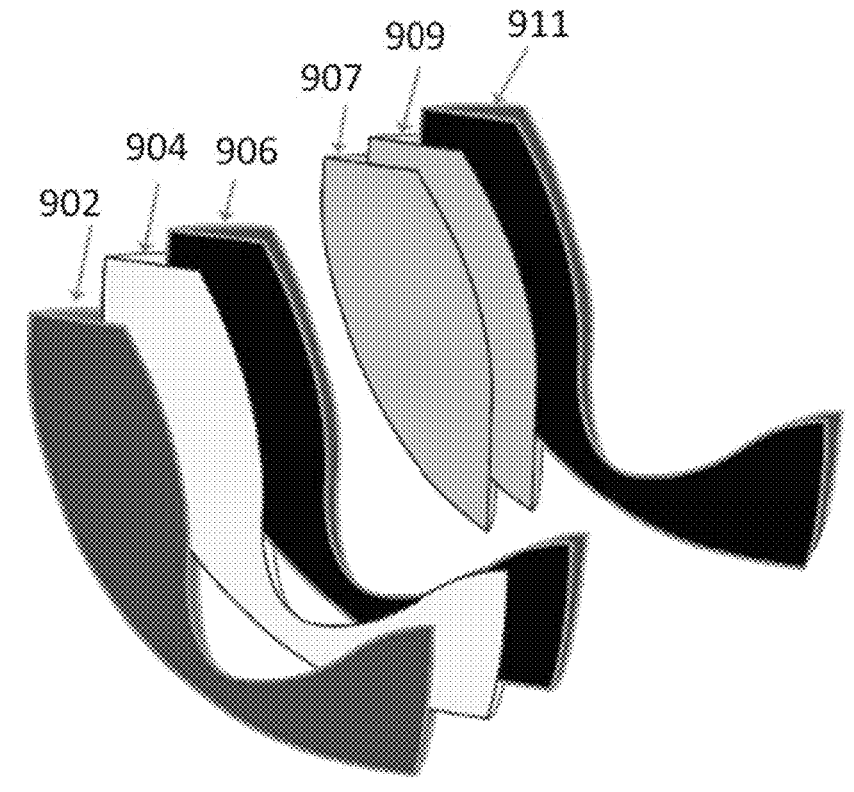
Figure 9a
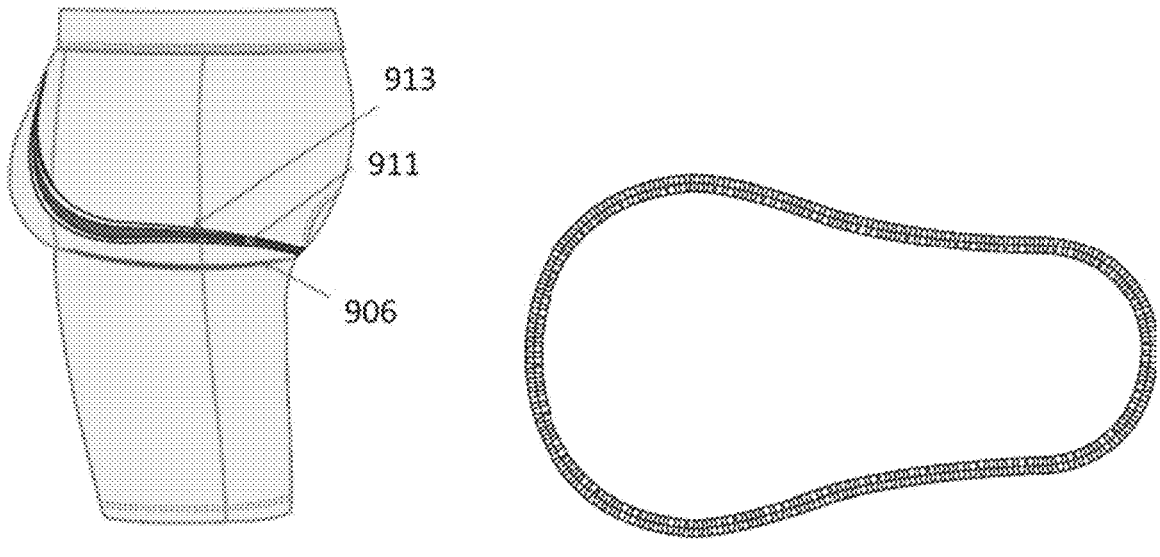
Figure 9b
Figure 9c

QUICK DRYING MOISTURE MANAGEMENT PANT

FIELD OF THE INVENTION

The invention relates to improved moisture management pant undergarments which are quick drying.

BACKGROUND

Disposable moisture management pant undergarments including nappies, underpants and briefs are an environmental problem of concern. Consumers are interested in more eco-friendly products such as reusable sanitary and incontinence products, including nappies and incontinence underwear products. Cloth nappies or diapers for infants and children have become popular in recent years. However, such reusable products have drawbacks including frequent leaking, especially at night-time. While booster systems are available for some cloth nappy or underwear products, they often slip or move around during use and can even slide out of the garment, soiling the wearer, clothing and even bedding at times. Many existing booster systems are limited in terms of additional volume capacity. Often, adult incontinence products tend to be bulky and unsightly and may also struggle to manage the larger volumes of moisture associated with incontinence.

While existing cloth solutions are launderable, due to the tendency of faeces to deeply embed into the fabric fibres, they tend to stain quickly, and odours are hard to remove and require quite harsh laundering conditions, particularly involving high temperatures and/or soaking with bleach or other oxidising products.

Drying after laundering can also be a challenge, as drying can be slow due to the nature of the products which means the products can acquire a musty smell and a greater number of garments overall is required to ensure a ready supply of useable product is to hand at all times due to the slow drying process.

US2021100698A1 describes a brief panty which has an envelope structure fixed (not floating) to a stretchable ribbed-fabric crotch portion. An optionally launderable absorbent pad can be placed into the envelope. US '698 does not recognise let alone deal with improving drying time or booster pad slippage and instead solves the problem of leakage from absorbent pads which expand with wetting to a degree that the pads are displaced from a wearer's crotch in a way that allows leaks. In US '698, the elasticity/resistance of the ribbed fabric allows pad expansion while close contact between the expanded absorbent pad and the crotch region of a wearer is maintained.

U.S. Pat. No. 5,707,364A describes a diaper undergarment having an internal sling in the form of a pocketed cradle containing a central channel for receiving a removable absorbent pad. While U.S. '364 recognises the problem of slippage of pads in diapers, the problem is solved by inclusion of the sling/pocket feature to accommodate a removeable pad. Further, the pads in U.S. '364 can be partially unfolded for drying. Nonetheless, separate laundering of the undergarment and absorbent pad are required, causing inconvenience the wearer having to fold and insert a pad into each garment prior to being worn. Bunching, curling and misshaping of the separate absorbent pad may also occur when it is subjected to washing that may compromise the security of its fit when placed in the undergarment pocket.

Notwithstanding the above, improved moisture management pants and/or pant undergarments which address one or more of the above problems or provides a useful alternative are desirable.

STATEMENTS OF THE INVENTION

According to a first aspect of the present invention, there is provided a launderable moisture management pant undergarment for wicking bodily fluid away from a wearer's skin into a fluid trapping core component of the pant undergarment, the undergarment comprising:

a pant body comprising leg openings having a crotch panel disposed therebetween, wherein at least a portion of the crotch panel is overlaid with a floating liner assembly partially fixedly attached to the pant body, wherein the fluid trapping core component is permanently attached to the floating liner assembly which traps bodily fluid wicked away from the wearer's skin, wherein at least a portion of the floating liner assembly is detached from to the pant body to allow physical separation of the floating liner assembly from the crotch panel to aid drying of the fluid trapping core component.

Suitably, the fixture of the floating liner assembly to the pant body may be a permanent fixture such that the floating liner assembly cannot be removed or extracted from the pant body by the user in normal operations/use of the undergarment. Advantageously, this means that the floating liner is a permanent feature of the undergarment such that it cannot be lost or exchanged for a different floating liner from another undergarment.

It will be understood that the portion of the floating liner assembly that is detached from the pant body is, during drying, intended to be arranged so as to be free of contact with the crotch panel of the pant body. This means the floating liner assembly and crotch panel are physically positioned away from each other to aid drying through enhanced drying air contact particularly with the fluid trapping core component. In use, this involves the user, after laundering the undergarment, gently pulling or teasing the wet floating liner assembly and the wet crotch panel away from each other while air drying. As used herein, the term "detached from" will be understood to be synonymous with "unattached to" in relation to the floating liner assembly and the pant body. The term "floating liner assembly" has the same meaning herein as "floating gusset liner assembly". In some embodiments, the pant body described herein may have two permanently formed leg openings. In other embodiments, such as in adaptive garments, the pant body described herein may have one permanently formed leg opening and one leg opening formed by joining opposing faces of the pant body or a waist portion thereof together, e.g., through clasps, hook and loop fasteners, press studs, or the like. In other embodiments, such as nappy garments, the pant body described herein may have two leg openings formed by joining opposing faces of the pant body or a waist portion thereof together, e.g., through clasps, hook and loop fasteners, press studs, or the like. The term "leg openings" will be understood to encompass these alternative embodiments.

As described herein, there is provided a moisture management pant undergarment for wicking bodily fluid away from a wearer's skin into a fluid trapping core component of the undergarment, the garment comprising a pant body having a waist portion, a front panel and a back panel connected by a pair of side wings, and a pair of leg openings having a crotch/gusset panel disposed therebetween, wherein at least a portion of the crotch/gusset panel is overlaid with a floating liner/gusset fixedly attached to the pant body and adapted to accommodate the fluid trapping core component which traps bodily fluid wicked away from the wearer's skin, wherein at least one or more portions of the floating liner/gusset and the crotch/gusset panel are physically separable from each other to expose the fluid trapping core component to aid drying.

As used herein, the term "floating liner assembly" shall be understood being synonymous with the term "floating liner/gusset". As used herein, the term "crotch panel" shall be understood as being synonymous with the term "crotch/gusset panel".

Desirably, the floating liner assembly is partially fixedly attached to the pant body enabling physical separation of the floating liner assembly and the crotch panel.

Desirably, at least one or more portions of the floating liner assembly are unattached to the pant body allowing physical separation of the fluid trapping core component from the crotch panel. Suitably, the floating liner is attached at one end to the front panel of the pant body and attached at the opposing end to the back panel of the pant body. To clarify, it is the portion of the liner/gusset around the leg region that is unattached to the pant body.

Advantageously, physical separation of these components allows drying air to better access the fluid trapping core component which can hold significant amounts of moisture and can be a challenge to air dry rapidly for that reason, particularly when moisture absorbent core fabrics are used. By enabling physical separation of the majority of the floating liner assembly, the improved access to drying air dramatically improves the air-drying times of these products. Faster drying products are more favoured by the consumer and also are associated with reduced risk of mould growth and malodors. At the same time, given the permanently fixed attachment to the pant body, it is impossible to lose or misplace the floating liner assembly component and the fluid trapping core component associated with the floating liner assembly.

Desirably, at least a portion of the crotch panel includes a moisture barrier component to prevent moisture leaking outside the pant during use.

As described herein, there is provided a removeable moisture management booster pad for use with a pant undergarment according the first aspect, wherein the booster pad comprises a fluid trapping core component, and an external covering surrounding the core component and comprising a moisture wicking fabric.

According to a second aspect of the present invention, there is provided a launderable moisture management pant undergarment for wicking bodily fluid away from a wearer's skin into a fluid trapping core component of the pant undergarment, the undergarment comprising:

a pant body comprising leg openings having a crotch panel disposed therebetween, wherein at least a portion of the crotch panel is overlaid with a floating liner assembly partially fixedly attached to the pant body, wherein the fluid trapping core component is permanently attached to the floating liner assembly which traps bodily fluid wicked away from the wearer's skin, wherein at least a portion of the floating liner assembly is detached from the pant body to allow physical separation of the floating liner assembly from the crotch panel to aid drying of the fluid trapping core component; and further comprising a removeable moisture management booster pad, wherein the booster pad comprises a fluid trapping booster core component sandwiched between layers, preferably two layers, of a moisture wicking fabric booster component.

Preferably, the moisture wicking fabric component comprises cotton, wool, particularly Merino wool, wicking polyester, wicking polypropylene, wicking nylon, wicking micromodal, or wicking bamboo. In some preferred embodiments, e.g., a toilet training underpant, the moisture wicking fabric component may be a cotton, or a cotton blend such as cotton elastane jersey, which may have a brushed or unbrushed (substantially smooth surface). Advantageously, as cotton is less wicking the other materials mentioned, such fabrics leaves a slightly wetter sensation which is less comfortable for the user which would benefit wearer who is undergoing toilet training for example. Cotton would be less preferred in the case where the user is a toilet trained individual. Preferably, the moisture wicking fabric is a brushed fabric, or otherwise textured surface having fibers displaced from the fabric knit, preferably a brushed polyester fabric. Desirably, the moisture wicking fabric of the booster pad is the same as the moisture wicking fabric of the pant undergarment of the first aspect. Suitably, the moisture wicking fabric booster component comprises a brushed fabric having a brushed or otherwise textured surface having fibers displaced from the fabric knit, preferably a brushed polyester fabric. The removeable moisture management booster pad is preferably launderable.

According to a third aspect of the present invention, there is provided a kit comprising:

(i) one or more a launderable moisture management pant undergarments for wicking bodily fluid away from a wearer's skin into a fluid trapping core component of the pant undergarment, the undergarment comprising:

a pant body comprising leg openings having a crotch panel disposed therebetween, wherein at least a portion of the crotch panel is overlaid with a floating gusset liner assembly partially fixedly attached to the pant body, wherein the fluid trapping core component is permanently attached to the floating liner assembly which traps bodily fluid wicked away from the wearer's skin, wherein at least a portion of the floating liner assembly is detached from to the pant body to allow physical separation of the floating liner assembly from the crotch panel to aid drying of the fluid trapping core component;

(ii) one or more removeable moisture management booster pads, each booster pad comprising a fluid trapping booster core component sandwiched between layers, preferably two layers, of a moisture wicking fabric booster component.

As described herein, there is provided a kit comprising:

(i) one or more moisture management pant undergarments for wicking bodily fluid away from a wearer's skin into a fluid trapping core component of the undergarment, each garment comprising a pant body having a waist portion, a front panel and a back panel connected by a pair of side wings, and a pair of leg openings having a crotch/gusset panel disposed therebetween, wherein at least a portion of the crotch/gusset panel is overlaid with a floating liner fixedly attached to the pant body and adapted to accommodate the fluid trapping core component which traps bodily fluid wicked away from the wearer's skin, wherein at least one or more portions of the floating liner and the crotch/gusset panel can be physically separated from each other to expose the fluid trapping core component to aid drying;

(ii) one or more removeable moisture management booster pads, each comprising a fluid trapping core component and an external covering surrounding the core component, the covering comprising a moisture wicking fabric.

Suitably, the moisture wicking fabric of the booster pad is the same as the moisture wicking fabric of the pant undergarment of the first aspect. Preferably, the moisture wicking fabric of the booster pad and the pant undergarment comprises a brushed fabric or otherwise textured fabric surface as defined herein.

In some embodiments, the external covering surrounding the core component of the booster pad comprises a brushed fabric or otherwise textured fabric surface having fibers displaced from the fabric knit. In some embodiments, one or more of the floating liner assembly and the crotch panel may also comprise the brushed fabric or otherwise textured fabric surface having fibers displaced from the fabric knit. In certain preferred embodiments, both the floating liner assembly and the crotch panel comprise the brushed fabric or otherwise textured fabric surface having fibers displaced from the fabric knit, as this will prevent the floating liner from slipping around during use.

In other embodiments, the external covering surrounding the core component of the booster pad and the floating liner and/or the crotch panel comprises a brushed fabric or otherwise textured fabric surface having fibers displaced from the fabric knit. In some embodiments, the external covering surrounding the core component of the booster pad comprises a fabric knit comprising a brushed or textured surface having fibers displaced from the fabric knit. In other embodiments, the external covering surrounding the core component of the booster pad and the floating liner and/or the crotch panel comprises a fabric knit comprising a brushed or textured surface having fibers displaced from the fabric knit. A brushed or otherwise textured surface having fibers displaced from the fabric knit is one in which the fibers of the fabric have been pulled out or teased out from the knit of the fabric, typically by brushing. It has been found that brushed fabrics alleviate many problems such as slippage of boosters inside undergarments and consequential moisture leakage and have also been found to provide a non-stick surface in terms of faeces, whereby faeces more readily can be scraped or brushed off the fabric. Brushed fabrics are described herein and include a brushed polyester fabric and a brushed polyester composite fabric. Suitably, the moisture wicking fabric is a brushed polyester composite fabric. In one embodiment, a preferred brushed polyester composite is a "polybrush", for example, a polyester and spandex polybrush composite, which preferably contains more than 50% polyester and less than 50% spandex, more particularly contains about 87% polyester and about 13% spandex or about 85% polyester and about 15%. Further aspects of the invention appear below in the detailed description of the invention.

BRIEF DESCRIPTION OF THE DRAWINGS

Embodiments of the invention will herein be illustrated by way of example only with reference to the accompanying drawings in which:

FIG. 3 illustrates a rear view of the fold up nappy of FIG. 1, which in this figure is shown in the folded configuration;

FIG. 4 illustrates the front panel of the fold up nappy of FIG. 1, when the nappy is in the unfolded configuration;

FIG. 5a illustrates a top down view of a fold up nappy of FIG. 1 in a flat or unfolded configuration without a booster pad; FIG. 5b illustrates a top down view of a fold up nappy of FIG. 1 in a flat or unfolded configuration with booster pad provided and sitting on top of the floating liner assembly in the crotch region of the nappy;

FIG. 6a illustrates an exploded view of the components of an example of a floating liner of the invention; FIG. 6b illustrates an exploded view of the components of an example of a booster pad of the invention for use with a nappy;

FIG. 9a illustrates an exploded view of the fabric arrangement for a men's trunk style gusset layering, FIG. 9b illustrates a left side on view of the full men's trunk with polybrush lined floating liner and polybrush lining in the crotch region to stop slippage of the floating liner in use, FIG. 9c illustrates a booster pad for men's undergarments with additional volume capacity to on end of the pad.

DETAILED DESCRIPTION OF THE INVENTION

Figure 1:
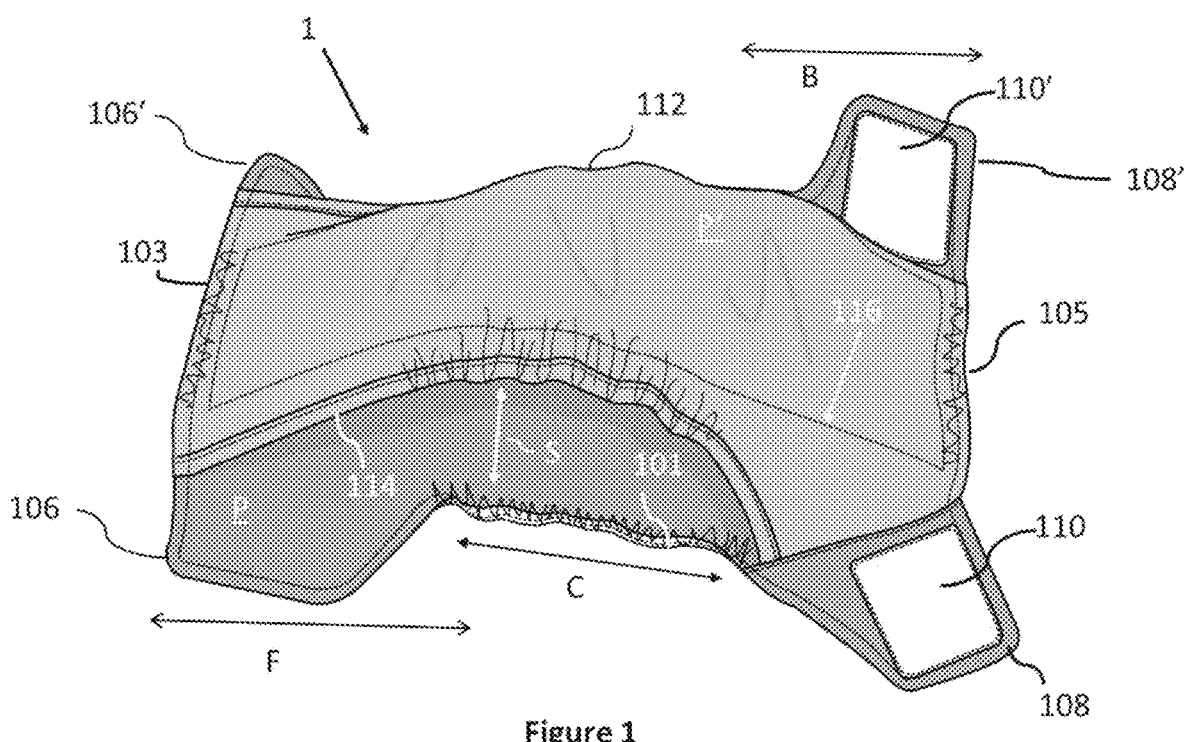
FIG. 1 illustrates one example of a moisture management pant/undergarment of the invention in the form of a fold up nappy which in this figure is shown in the flat or unfolded configuration in which the floating liner assembly is shown physically separated from the crotch panel of the nappy.

Although it is known to provide separately launderable absorbent pads for undergarments to facilitate drying of the high-moisture holding component of the undergarment, such arrangements also suffer several disadvantages, including giving rise to an additional burden of separate articles that must be washed, may be lost, user time spent folding and preparing garments for wear, and potential movement of, or instability in the position of, the absorbent pad in the crotch region of a garment. The present invention surprisingly overcomes both these disadvantages. Firstly, it provides a moisture management pant undergarment that is launderable but also contains a permanently attached fluid absorbing core component that is resistant to movement and slippage. Secondly, it recognises, for the first time, that a launderable garment containing a reusable and permanently attached fluid trapping core component must be capable of absorbing bodily fluid, and potentially significant volumes of bodily fluid such as urine, from a wearer, but also be hygienically and easily launderable, including being able to dry effectively after washing. Existing launderable garments with removable inserts have not needed to address the problem of differential drying of the shell and absorbent insert components, as the components in such garments were designed to be separated. However, the present inventors have discovered that a floating liner assembly having a permanently attached fluid trapping core component that is only partially attached to the pant body of the undergarment allows both security of position of the fluid trapping core for a user when worn, but also allows physical separation of the floating liner assembly from the crotch panel to aid drying of the fluid trapping core component when the undergarment is wet after laundering.

Other undergarments known in the art have overcome the issue of absorbent pad movement by permanently fixing a fluid absorbing pad in place in the crotch region of the undergarment. However, as discovered by the present inventors, such solutions can give rise to previously unappreciated problems in the field of incontinence and nappy wear in particular, where a permanently attached absorbent component must be capable of absorbing significant volumes of bodily fluid, such as urine, and commonly also faeces, from a wearer, but at the same time be hygienically and easily launderable, including being able to dry effectively after washing. In recognising this problem, the present inventors have devised a solution especially required in launderable undergarments capable of very high moisture management levels, but that is also beneficial to launderable undergarments capable of lower, such as low, moderate or high, moisture management levels. The solution involves the launderable garment containing a fluid trapping core component permanently attached to a floating liner that is only partially attached to the pant body of the undergarment allowing physical separation of the floating liner assembly from the crotch panel, which allows washing water better accessibility to the soiled fluid trapping core component and allows for a more rapid drying rate of the fluid trapping core component during laundering without compromising its bodily fluid-absorbing capacity.

Thus in one aspect, the invention relates to an improved moisture management pant undergarment for wicking bodily fluid away from a wearer's skin into a fluid trapping core component of the undergarment. Suitably, the pant undergarment is a launderable moisture management pant undergarment. The pant undergarment wicks bodily fluid away from a wearer's skin into a non-removeable fluid trapping core component of the pant undergarment. In one embodiment, the undergarment comprises a pant body comprising leg openings having a crotch panel disposed therebetween. Desirably, at least a portion of the crotch panel is overlaid with a floating liner assembly. Suitably, the floating liner assembly may be partially fixedly attached to the pant body. It will be understood that the floating liner assembly accommodates a non-removable fluid trapping core component which traps bodily fluid wicked away from the wearer's skin. To derive the advantages of the invention, at least a portion of the floating liner assembly is unattached to the pant body. This allows physical separation of the floating liner assembly from the crotch panel to aid drying of the fluid trapping core component while the undergarment is wet after laundering.

In some embodiments, the pant undergarment comprises a front panel, a back panel, and a crotch panel, and one or more of the front panel, the back panel, and the crotch panel comprise a moisture barrier component to prevent moisture leaking outside the pant during use. It will be understood during use, the moisture barrier component is distal to a wearer's skin. Desirably, the pant undergarment comprises a front panel, a back panel, and a crotch panel, and wherein one or more of the front panel, the back panel, and the crotch panel are lined on an inner surface with a moisture wicking fabric, the inner surface being proximal to the wearer's skin in use, preferably wherein the moisture wicking fabric overlies a moisture barrier component.

The moisture management pant undergarment of the invention may be capable of managing very high moisture levels due to its design which may utilise a number of layers of absorbent fluid trapping fabric, preferably microfibre terry fabric, of a fluid trapping core component provided in and around the crotch panel/region of the undergarment and/or as a part of a booster pad. The absorbent fluid trapping fabric is used in the form of a fabric fluid trapping core of at least 1, at least 2, at least 3, at least 4 or at least 5 layers of the absorbent fluid trapping fabric. In some embodiments, the absorbent fluid trapping fabric is present in the fabric trapping core as up to 5 layers but no more of the absorbent fluid trapping fabric.

Where required, additional moisture management capability can be provided by including a compatible removeable moisture management booster pad insert which is provided to the crotch region of the undergarment, where such booster pad preferably comprises multiple layers of an absorbent fluid trapping fabric, preferably an absorbent microfibre terry fabric. Suitably, the booster pad is washable and reusable. Suitably, the booster pad is launderable.

Suitably, to reduce problematic slippage of the booster pad which can occur due to movement of the wearer, preferably the booster pad and the crotch panel and/or the floating liner assembly of the undergarment may be separately provided with surfaces/linings that are compatible together in terms of reducing slippage. For example, a preferred removeable moisture management booster pad for positioning over the crotch panel and/or the floating liner assembly preferably has an external covering surrounding its fluid trapping core component, the covering comprising a moisture wicking fabric having a brushed or otherwise textured fabric surface having fibers displaced from the fabric knit, wherein contact between a surface of the crotch panel and/or floating liner assembly and a surface of the moisture wicking fabric of the booster pad results in a friction or interference fit between the booster pad and crotch panel/floating liner assembly when also provided with a brushed or otherwise textured fabric surface. This friction fit sticks the component parts together to form a non-slip arrangement whereby the booster pad is much more securely fixed in position than in an equivalent underwear garment without compatible surfaces/linings.

Suitably, the moisture wicking fabric is a brushed fabric having a brushed or otherwise textured surface having fibers displaced from the fabric knit, such as a brushed wool, particularly brushed Merino wool, a brushed wicking polyester, a brushed wicking polypropylene, a brushed wicking nylon, a brushed wicking micromodal, a brushed wicking bamboo, a brushed cotton, or composites thereof. In some other examples, where for example, a toilet training pant is desired, a cotton or cotton blend fabric (typically having a smooth or unbrushed surface) is used instead of the brushed or textured fabric. Suitable examples of cotton or cotton blend fabrics include cotton and cotton blends such as cotton elastane jersey. The advantages of these fabrics for training pants are described elsewhere herein. In another embodiment, the moisture wicking fabric may be a bamboo fabric, such as bamboo fleece. In yet further embodiments, the moisture wicking fabric may be a biodegradable bamboo fabric, such as biodegradable bamboo fleece.

In some embodiments, the moisture wicking fabric is a brushed fabric comprising a brushed polyester or a brushed polyester composite, preferably containing more than 50% polyester and less than 50% spandex. Desirably, the moisture wicking fabric is a brushed polyester composite comprising about 87% polyester and about 13% spandex.

Furthermore, while cloth-based heavy duty moisture management pant undergarments such as cloth nappies and cloth incontinence underwear are known, while such cloth solutions are launderable, due to the tendency of faeces to deeply embed into the fabric fibres, they tend to stain quickly, odours are difficult to remove and they require quite harsh laundering conditions particularly involving high temperatures and/or soaking with bleach or other oxidising products. Such conditions can lead to premature failure of the garments in terms of protection from leakage. Use of the brushed or otherwise textured fabric alleviates this problem.

Furthermore, drying such garments after laundering can also be a challenge as drying can be slow due to the nature of the products which means the products can acquire a musty smell and more products overall are required to ensure a ready supply of useable product is to hand at all times. This is particularly the case for undergarments supporting very high moisture management capabilities as they hold significant amounts of moisture when wet after laundering, but may also apply to low, moderate or high moisture management capability garments comprising moisture absorbent fluid trapping cores, and especially multi-layer fluid trapping absorbent cores. Indeed, the degree of slow drying only became evident during design of the launderable, reusable moisture management pant undergarments such as nappy and incontinence undergarments as described herein which have multiple layers of fluid absorbing fabric in their cores. Such a problem has not been anticipated or recognised in prior art solutions to the problem particularly of high moisture management undergarments, such as is required for nappies and incontinence underwear. To address the problems relating to drying such as length of drying time, musty odours etc., which may be particularly associated with drying of high moisture capability undergarments, the present invention was provided with a unique design feature that conveniently aids drying time and so avoids the undesirable problems described above. This design feature offers the same benefit of aiding drying time to other absorbent-core containing garments, including period underwear designed for absorption of menstrual blood. This design feature comprises building the fluid trapping core component into the garment in a way that better enables air to access the fluid trapping core component while the garment is being dried after laundering. Thus, the improved moisture management pant undergarment of the invention is provided with a floating liner assembly in the crotch portion of the undergarment which is permanently attached to the undergarment yet is largely physically separable from the crotch panel of the pant undergarment. After laundering, when the liner is physically lifted/separated from the crotch panel, there is much improved access to drying air to dramatically speed up drying time. This enhances the practical day to day useability of the products and means the user can rely on fewer products overall for day-to-day use. In one embodiment, an improved moisture management pant undergarment comprises a pant body having a waist portion, a front panel and a back panel. The waist portion may be attached to both the front and back panels. In one embodiment, an improved moisture management pant undergarment comprises a pant body having a waist portion, a front panel and a back panel connected by a pair of side wings, and a pair of leg openings having a crotch panel disposed therebetween, wherein at least a portion of the crotch panel is overlaid with a floating liner fixedly attached to the pant body and adapted to accommodate the fluid trapping core component which traps bodily fluid wicked away from the wearer's skin, wherein at least one or more portions of the floating liner and the crotch panel can be physically separated from each other to expose the fluid trapping core component to aid drying.

Suitably, the floating liner assembly is permanently attached at one end to a front panel of the pant body and permanently attached at an opposing end to a back panel of the pant body.

Desirably, the floating liner assembly has opposing short edges and opposing long edges, preferably wherein the opposing long edges of the floating liner assembly are unattached to the pant body. Suitably, long edges of the floating liner assembly proximate the leg openings of the pant body are elasticated.

Desirably, at least one or more portions of the floating liner are unattached to the pant body allowing physical separation of the fluid trapping core component from the crotch panel. It will be understood that at least one edge, at least two edges but most preferably two of the floating liner assembly edges are physically attached to the pant underwear. While one long edge (corresponding to the edge adjacent the leg opening region) can be unattached, it is preferred that two long edges (corresponding to the edges adjacent the leg opening region) are unattached to the pant underwear to allow optimum physical separation. The ability to physically separate and break physical contact between the floating liner from the crotch panel advantageously provides a gap and/or space to allows air to circulate around the fluid trapping and wicking components of the undergarment which aids drying after laundering. This is particularly important in a pant underwear garment which uses the very high absorbency fluid trapping core used herein which has significantly more moisture absorbency compared to prior art solutions. It is also beneficial when used in other bodily fluid absorbing applications, such as period underwear, which may be capable of absorbing significant volumes of menstrual blood. As air can access the fluid trapping core component more easily compared to an equivalent article without the floating liner of the invention, as confirmed by test data provided herein, the pant undergarment has significant advantages in terms of greater speed and more convenient laundering and/or drying. Likewise, during washing, improved water and detergent access to the fluid trapping core component means more efficient and faster laundering.

Suitably, the floating liner assembly is permanently attached at one end to a front panel of the pant body and permanently attached at an opposing end to a back panel of the pant body.

A preferred floating liner has opposing short edges and opposing long edges, preferably wherein the opposing long edges of the floating liner assembly are unattached to the pant body. Suitably, long edges of the floating liner assembly proximate the leg openings of the pant body are elasticated.

The opposing long edges are located around the area of the leg opening in the crotch region of the garment. Desirably, the floating liner is attached at one end to the front panel of the pant body and attached at the opposing end to the back panel of the pant body. Suitably, the short edges of the floating liner are attached at one end to the front panel of the pant body and attached at the opposing end to the back panel of the pant body. Preferably, the short edges of the floating liner are attached at one end to a front portion of a gusset of the pant body and attached at the opposing end to a back portion/area of the gusset of the pant body. In one embodiment, one short edge of the floating liner assembly is attached to the pant underwear, corresponding to an edge adjacent the front panel or back panel of the pant underwear. In another embodiment, two short edges of the floating liner assembly are attached to the pant underwear, corresponding to one short edge adjacent the front panel and one short edge adjacent the back panel of the pant underwear. Desirably, long edges of the floating liner are unattached to the pant body around the leg opening region. This enables good separation between the floating liner assembly and crotch panel of the pant undergarment during laundering. This also advantageously ensures good stability of the floating liner assembly in the crotch region of a wearer during use.

Suitably, the fluid trapping core component is attached to an underside of the floating liner assembly, the underside being distal to a wearer's skin in use.

Suitably, at least a portion of the floating liner assembly comprises a fluid wicking fabric for contacting a wearer's skin in use. Desirably, the portion of the floating liner assembly comprising the fluid wicking fabric is a top side of the floating liner assembly, the top side being adjacent a wearer's skin in use.

Suitably, the pant undergarment is in the form of a launderable nappy, a launderable incontinence brief, launderable incontinence underwear, a launderable incontinence trunk, launderable incontinence pantyhose, launderable incontinence leggings, launderable incontinence gym shorts, a launderable toilet-training garment, launderable adaptive underwear or launderable tween/teen incontinence underwear. The pant undergarment may also be in the form of a girls or boys teen/tween incontinence underwear, or adaptive styles for those with disabilities. The pant undergarment may also be in the form of a launderable period management garment, such as a launderable period management brief, launderable period underwear, a launderable adaptive period management brief, launderable period management shorts, launderable period management pantyhose, or launderable period management leggings. In one embodiment, the pant undergarment as described herein is not a launderable period management garment. In one embodiment, the pant undergarment as described herein is a launderable nappy or a launderable incontinence garment. In one embodiment, the pant undergarment as described herein is a launderable nappy, a launderable incontinence garment, or a launderable period management garment.

Suitably the pant undergarment may be provided in a pull up conformation or a foldable configuration for folding into a wearable pant undergarment. Desirably in the foldable configuration, each side of a back panel or optionally a waist portion attached to pant body comprises a fastening portion configured to reversibly attach to a front panel, which, when attached, forms a waist opening. Suitably, the fastening portion is in the form of a side wing.

Suitably, the long edges of the floating liner are elasticated, particularly in a nappy or incontinence pant where extra protection and security from leaks is desired.

Preferably the fluid trapping core component is permanently attached to the floating liner, preferably to the underside of the floating liner. However, in some embodiments, the fluid trapping core component may be removably attached to the floating liner.

Desirably, the fluid trapping core component is attached to an underside of the floating liner assembly. "Underside" in this context refers to being positioned distal with respect to a wearer's skin in use. For example, the fluid trapping core component may be attached by stitching or adhesive to the floating liner assembly. In other embodiments, the the fluid trapping core component may be attached to the floating liner by insertion into a pocket provided in the floating liner. Thus preferably the fluid trapping core component is in a pocket provided in the floating liner assembly. Conveniently, this may allow the fluid trapping core component to be replaced without removal of the garment, for example at night-time when the wearer is asleep or at other times when removal of the garment is not possible. However, it is preferred that the fluid trapping core component be permanently attached to the floating liner assembly. In embodiments where the fluid trapping core component is inserted in a pocket provided in the floating liner assembly, permanent attachment of the fluid trapping core component may be by means stitching, adhesive, or other means of attachment of the fluid trapping core component inside the pocket, either to one or more faces or one or more edges of the pocket, or may be by sealing the pocket at its edges by stitching, adhesive, or other means with the fluid trapping core component already inside it, such that the fluid trapping core component is unable to be removed from the pocket.

In some embodiments, a second fluid trapping core component may be attached to an upper side of the crotch panel, for example by stitching or adhesive or through use of a pocket provided in the region of the crotch panel. Preferably, the second fluid trapping core component is permanently attached to the crotch panel. However, in some embodiments, the second fluid trapping core component may be removably attached to the crotch panel. Suitably, in such embodiments, the fluid trapping core component is attached by insertion into a pocket provided in the crotch panel.

In some embodiments, a second fluid trapping core component is attached to an upper side of the crotch panel, the upper side of the crotch panel being proximal to the wearer's skin in use. Desirably, wherein the second fluid trapping core component is permanently attached to the upper side of the crotch panel or the second fluid trapping core component is removably attached to the crotch panel. If desired, the second fluid trapping core component is in a pocket provided in the crotch panel.

Suitably, the fluid trapping core component and/or the second fluid trapping core component comprises one or more layers of one or more layers of an absorbent, quick drying fabric, preferably an absorbent, quick drying microfibre fabric such as a polyester microfibre fabric or an absorbent, quick drying fabric manufactured from a cellulosic material, preferably hemp, bamboo. In some embodiments, the fabric is a biodegradable, biobased, or compostable version of any of the aforementioned fabrics. Desirably, the fluid trapping core component and/or the second fluid trapping core component comprises a microfibre towelling comprising greater than 50% polyester and less than about 50% polyamide or a microfibre towelling that is a bamboo terry as this material will be biodegradable/compostable in active soil. Suitably, the fluid trapping core component and/or the second fluid trapping core component comprise a microfibre towelling comprising about 80% polyester and about 20% polyamide. In some embodiments, the fluid trapping core component and/or the second fluid trapping core component comprises an absorbent, quick drying fabric manufactured from a cellulosic material, preferably hemp, bamboo, or cotton. In some embodiments, the fluid trapping core component and/or the second fluid trapping core component described herein comprise a synthetic fabric (derived from manmade fibres), a semi-synthetic fabric (derived from at least some fibres/raw materials that are of natural origin, e.g., cellulosic fibres) or a natural fabric (derived from fibres of 100% natural origin). Semi-synthetic fabrics refer to those fabrics being synthetically modified derivatives of a natural fabric, and include fibres such as Modal®. In a preferred embodiment, the fluid trapping core component comprises one or more layers of an absorbent, quick drying fabric, preferably an absorbent, quick drying microfibre fabric such as a bamboo terry, a polyester, a recycled polyester or biodegradable polyester or a biobased polyester, or a polyester composite microfibre fabric, such as a polyester/polyamide blend. In one embodiment, the fluid trapping core component comprises a microfibre fabric comprising a polyester/polyamide blend, such as 90% polyester/10% polyamide, or 85% polyester/15% polyamide, or 80% polyester/20% polyamide, or 70% polyester/30% polyamide. In some embodiments, the polyester is a recycled polyester. In some embodiments, the polyamide is a recycled polyamide. In some embodiments, the fluid trapping core component comprises a microfibre fabric comprising recycled polyester/recycled polyamide blend, such as 90% recycled polyester/10% recycled polyamide, or 85% recycled polyester/15% recycled polyamide, or 80% recycled polyester/20% recycled polyamide, or 70% recycled polyester/30% recycled polyamide. As used herein, the term "biodegradable" is used in the sense of being at least 80% compostable but more preferably at least 95% to 100% compostable in active soil in 5 years or less, preferably in 4 years or less, preferably in 3 years or less, more preferably in 2 years or less, and most preferably in 1 year or less. Active soil comprises typical soil microbes including bacteria and fungi. As used herein, the term "compostable" refers to materials that readily break down quickly and safely in a composting system through the action of microbial activity in a defined time period to form compost or humus comprising natural materials only which cause no harm to the environment. As used herein, the term "biobased" refers to the source of raw materials for the fabric being plant-based rather than fossil-fuel based. Desirably, the fluid trapping core component comprises an absorbent, quick drying fabric, for example, manufactured from a cellulosic material, preferably hemp, bamboo, or cotton which are more environmentally friendly. Accordingly, in some embodiments, the fluid trapping core component may comprise a partly or fully bio-based absorbent quick drying fabric, a biodegradable absorbent quick drying fabric, or a compostable absorbent, quick drying fabric. Desirably, the fluid trapping core component comprises at least one layer of fabric, or at least two layers of fabric, or at least three layers of fabric, or at least four layers of fabric, or at least five layers of fabric, or at least six layers of fabric, or at least seven layers of fabric, or at least eight layers of fabric, or at least nine layers of fabric, or at least ten layers of fabric. Each layer of fabric can be the same or different or a mixed combination of fabrics. In a preferred embodiment, the fluid trapping core component comprises three layers of fabric.

In some embodiments, at least a portion of the crotch panel includes a moisture barrier component to prevent moisture leaking outside the pant during use.

Desirably, in the fluid trapping core component, each layer of fabric has a weight or density in a range of 50 gsm to 500 gsm, more preferably between 150 gsm and 350 gsm, and most preferably 240 gsm or 280 gsm.

Preferably, the fluid trapping core component has a thickness of between 1 and 50 mm, preferably 1 and 30 mm, preferably 1 and 15 mm, more preferably 1 to 9 mm. It will be understood that the fluid trapping core component in a nappy or adult incontinence pants will be at the higher end, for example, greater than about 15 mm, depending on the number of absorbent fabric layers used, while in an underwear garment, the core component thickness less than 9 mm are preferred. Underwear garments herein may refer to period management underwear or incontinence underwear, including bladder leakage underwear.

Preferably, the fluid trapping core component of the booster when present has a thickness of between 1 and 30 mm, preferably 1 and 20 mm, preferably 1 and 15 mm, more preferably 1 to 9 mm or less than about 7 mm in underwear or briefs undergarment. In some embodiments, the fluid trapping core component and/or the second fluid trapping core component has a thickness of between 1 and 20 mm, more preferably 1 to 9 mm in a nappy undergarment. It will be understood that the fluid trapping core component in a nappy or incontinence product will be at the higher end, for example, around 8-20 mm, depending on the number of absorbent fabric layers used, while in an underwear garment, the core component thickness for the booster pad of less than about 9 mm, more preferably less than about 6 mm are preferred.

Preferably, the fluid trapping core component comprises at least one layer of a fabric having a weight or density in a range of 50 gsm to 500 gsm, more preferably between 150 gsm and 350 gsm, and most preferably 240 gsm or 280 gsm. In other embodiments, the moisture wicking fabric has a weight or density in a range of 100 gsm to 300 gsm, more preferably between about 150 gsm and about 250 gsm, and most preferably about 180 gsm or about 235 gsm.

Suitably, one or both of the fluid trapping core component and the second fluid trapping core component has a thickness of between 1 and 20 mm, preferably 1 and 15 mm, more preferably 1 to 9 mm or in underwear less than about 7 mm.

In embodiments using a fluid trapping core component of 500 gsm density, 5 layers of such fabric, will have a capacity of up to 500 mL of fluid. An undergarment fluid trapping core having three 3 absorbent layers each will 500 gsm allows accommodation of up to 1800 mL of fluid. When used together, such preferred booster pads of the invention comprising 5 absorbent layers and the preferred fluid trapping core component as described herein with 3 absorbent layers allows accommodation of significant amounts of fluid, up to about 2300 mL.

Preferred booster pads of the invention comprising 5 absorbent layers as described herein, preferably of a 280 gsm terry microfibre, may accommodate up to 250 mL of fluid. This is a useful capacity for the nappy booster in particular, but may also be useful in other pant undergarments as described herein, such as toilet training pants and/or child or adult incontinence pants. However, additional capacity can be added by adding more absorbent layers as required to the booster pad. Clearly more layers add additional bulk to the booster which may be undesirable in some garments.

Desirably, the pant undergarment further comprises an optional fluid trapping core component associated with the crotch panel of the pant undergarment which traps bodily fluid wicked away from the wearer's skin by the first moisture wicking fabric lining in the crotch panel region. This optional fluid trapping core component in the crotch panel of the undergarment may be referred to as a second fluid trapping core component, and in some embodiments, is permanently attached to the crotch panel of the undergarment. In some embodiments, the second fluid trapping core component is one component of a multi-component assembly provided directly on the crotch panel as distinct from the floating liner assembly. Where a second fluid trapping core component is provided in the crotch panel in addition to the fluid trapping core component of the floating liner assembly, the moisture holding capacity of the undergarment may be increased. The second fluid trapping core component may be as described herein for the fluid trapping core component in terms of fabric composition, number of layers, gsm of fabric layers, absorption capacity of individual and combined layers, etc. Inclusion of a second fluid trapping core component associated with the crotch panel of the pant undergarment may be desirable in certain embodiments, such as in toilet training pant undergarments.

Inclusion of a fluid trapping core component as described herein allows accommodation of significant amounts of fluid. For example, an undergarment fluid trapping core having three 3 absorbent layers, preferably of a 280 gsm terry microfibre, allows accommodation of up to 900 mL of fluid. This is a useful capacity for the nappy booster in particular. This is a useful capacity for the nappy liner/gusset in particular. However, additional capacity can be added by adding more absorbent layers as required to the fluid trapping core. The greater capacity of the undergarment fluid trapping core compared to the booster is due to the greater surface area of absorbent fabric used in the undergarment, particularly the nappy or incontinence product.

When used together, the preferred booster pads of the invention comprising 5 absorbent layers and the preferred fluid trapping core component as described herein allows accommodation of significant amounts of fluid, up to about 1150 mL in some embodiments.

Desirably, at least a portion of the crotch panel includes a moisture barrier component to prevent moisture leaking outside the pant during use. Suitably, one or more of the front panel, a back panel, side wings and crotch panel or region comprise a moisture barrier component. Most preferably, all of the front panel, a back panel, side wings and crotch panel comprise a moisture barrier component. Suitably in a nappy or certain incontinence products, all of the front panel, a back panel, side wings and crotch panel comprise the moisture barrier component. In contrast, in adult and kids "regular" (non-incontinence) underwear, the moisture barrier component may be confined to the crotch panel, for example, for aesthetic and/or comfort reasons.

Preferably, during use, the moisture barrier component is distal to a wearer's skin. Preferably, the moisture barrier component comprises a moisture proof fabric, a moisture resistant fabric or a moisture repellent fabric or a fabric treated to be moisture proof, moisture resistant or moisture repellent. Preferably, the moisture barrier component is a fabric which comprises a waterproof or water-resistant laminate film or a chemical coating, rendering the fabric moisture proof moisture resistant or moisture repellent. Antimicrobial and/or anti-odour treatments such as are known to the skilled person can used on one or more of the fabric components described herein.

Preferably, the moisture barrier component comprises a waterproof, water resistant or water repellent fabric or fabric treated to have such properties which prevents movement of bodily fluids from the fluid trapping core to outside the pant, thereby avoiding leakage of captured bodily fluid. Preferably, the moisture barrier component comprises a fabric which is itself waterproof, water resistant or water repellent. Desirably, the fabric may be treated with one or more agents for example, comprising hydrophobic polymers, such as polyethylene based hydrophobic polymers, hydrophobic non-fluorinated acrylic polymers, hydrophobic non-fluorinated urethanes, or bio-based or bio-derived hydrophobic polymers or compounds, (ideally not comprising fluorinated compounds such as PFOAs), which may assist with waterproofing, water resistance or water repellence. Suitable moisture barrier films can comprise water proof, water repellent agents, compounds or compositions such as those available from the companies Huntsman or Rudolf. A preferred agent used to treat fabric to impart waterproof or water resistance or water repellency include Aquapel™ by Nanotex which is a water repellent hydrocarbon based composition. Suitable moisture barrier films having inherent waterproofing or water resistance or water repellency are available from Ding Zing. It will be understood that the terms "moisture" and "water" is used herein in the sense that it encompasses bodily fluids, particularly, sweat, urine, discharge, and/or blood.

In some embodiments, the moisture barrier component comprises a polyester/polyurethane laminate fabric, preferably in the form of a cotton or polyester knit fabric bonded to a polyurethane breathable and waterproofing film, generally having a thickness of 1 mm or less. Preferred moisture barrier components are recycled and/or biodegradable, for example, recycled and/or biodegradable polyester and biodegradable polyurethane which may be laminated directly onto the fluid trapping core component, the crotch panel, the front panel, the back panel, and/or the side wings. In other embodiments, the moisture barrier component comprises a biodegradable and/or compostable polymer film alone, such as a thermoplastic polyurethane (TPU) film, e.g., available from Ding Zing. Such films can be used wherever water barrier function is required, for example, it can be laminated directly to the underside of the fluid trapping core component fabric.

Preferably, at least a portion of the floating liner assembly comprises a fluid wicking fabric. Preferably, the fluid wicking fabric is provided on skin facing side of the floating liner assembly. Direct contact with the skin allows any moisture to be quickly wicked away. The fluid wicking fabric functions to draw or wick moisture, e.g., sweat, urine, blood, quickly away from the wearer's skin and into the fluid trapping core component associated with the floating liner or the crotch panel of the pant underwear of the invention. Preferably, the inner surfaces of the pant undergarment are lined with a moisture wicking fabric, such as one or more of the front panel, the back panel, the side wings and/or the crotch panel are lined with a moisture wicking fabric. Preferably, the inner surfaces of each of the front panel, the back panel, and the crotch panel are lined with a moisture wicking fabric. Where present, side wings may also be lined with a moisture wicking fabric. Suitably in a nappy or certain incontinence products, all of the inner lining of the pant undergarment, such as the front panel, back panel, and crotch panel, comprise the moisture wicking fabric. Desirably, at least a portion of the crotch panel includes the fluid wicking fabric. However, in adult and kids "regular" (non-incontinence) underwear, the moisture wicking fabric may be confined to the crotch panel, for example, for aesthetic and/or comfort reasons.

For some component parts, e.g., the front panel, the back panel, and the crotch panel, and where present, the side wings, the moisture wicking fabric overlies the moisture barrier component.

Suitably, the moisture wicking fabric is wool, particularly Merino wool, wicking polyester, wicking polypropylene, wicking nylon, wicking bamboo (e.g. wicking bamboo fleece), or a cellulosic fabric such as wicking micromodal, or lyocell (brand name Tencel®). Preferably, the moisture wicking fabric is a brushed fabric. Desirably, the moisture wicking fabric is a brushed polyester or a brushed polyester composite fabric. A polybrush fabric is particularly preferred as it resists faeces embedding in the fibres and assist in use of an anti-slip booster pad. In some embodiments, the polybrush comprises a blend of polyester and elastane, such as 80% polyester/20% elastane, 85% polyester/15% elastane, or 90% polyester/10% elastane. In some embodiments, the polyester in the polybrush is recycled polyester, such as an 85% recycled polyester/15% elastane blend. In some embodiments, the elastane is biobased elastane, being wholly or in part derived from a natural source such as a plant source, e.g., corn. Polybrush and other similar desirable fabrics have a surface without excessive undulations and/or piling (particularly after laundering) and overall has a tighter knit and overall a smoother, more level pile appearance than for example fleece which is often used as a nappy liner material and into which faeces readily embeds. The properties of the polybrush, in particular, allow faeces to be readily removed from the fabric during washing which means less vigorous washing/temperature cycles are sufficient, prolonging the lifetime of the undergarment. In other embodiments, fabrics such as a cotton, or a cotton blend fabric such as cotton elastane jersey may be suitable as moisture wicking fabric. Such cotton or cotton based fabrics need not comprise a brushed or otherwise textured surface, i.e., they can be substantially smooth. In some embodiments, the cotton/elastane jersey is a knit comprising a blend of cotton and elastane, such as 80% cotton/20% elastane, 85% cotton/15% elastane, 90% cotton/10% elastane, etc. In some embodiments, the elastane is biobased elastane, being wholly or in part derived from a natural source such as a plant source, e.g., corn.

Suitably, the moisture wicking fabric has a weight or density in a range of about 100 gsm to about 300 gsm, more preferably between about 150 gsm and about 250 gsm, and more preferably still between about 215 gsm and about 245 gsm, most preferably about 235 gsm, particularly in the case of the nappy embodiment.

Preferably, the external portions of one or more of the front panel, the back panel, the side wings and the crotch panel comprise one or more shell fabrics. Preferably, each of the front panel, the back panel, the side wings and the crotch panel comprise a shell fabric. Suitable shell fabrics include polyester, nylon (or biodegradable/recycled versions thereof), cotton, hemp, Tencel, bamboo viscose or bamboo Lyocell, or blends of polyester, nylon (or biodegradable/recycled versions thereof), cotton, hemp, Tencel, bamboo viscose or bamboo Lyocell. It will be understood that such fabrics may include blends with elastane. In some embodiments, the elastane is biobased elastane, being wholly or in part derived from a natural source such as a plant source, e.g., corn. The shell fabric may be provided with any desired pattern or colour scheme that may be desired.

In preferred embodiments, the moisture barrier component is provided between the shell fabric and the moisture wicking fabric. For example, in one embodiment, the moisture barrier component may be provided as a laminated sheet disposed between the shell fabric and the moisture wicking fabric, such as in the form of a polyurethane laminate film. In other embodiments, the moisture barrier component may be provided as a laminated sheet sandwiched between two layers of the shell fabric. Desirably, moisture barrier component comprises a polyester/polyurethane laminate fabric, preferably in the form of a polyester knit fabric bonded to a polyurethane breathable and waterproofing film, generally having a thickness of 1 mm or less. In some embodiments, the moisture barrier component may comprise two layers of a polyester sandwiching a polyurethane laminate layer. In other embodiments, the moisture barrier component may be in the form of a polyurethane film, preferably a biodegradable/compostable thermoplastic polyurethane such as those available under the Ding Zing supplier/brandname. Such films avoid the need for polymer laminated fabrics which may be less breathable and/or environmentally friendly.

The invention also extends to a removeable moisture management booster pad for use with a pant undergarment of the first aspect, the booster pad comprises a fluid trapping core component and an external covering surrounding the core component and comprising a moisture wicking fabric. Suitably, the moisture wicking fabric of the external covering comprises wool, particularly Merino wool, cotton, a cotton blend such as cotton elastane jersey, wicking polyester, wicking polypropylene, wicking nylon, wicking micromodal, or wicking bamboo, or any one of the aforementioned fabrics blended with elastane. In one embodiment, fabrics such as a cotton elastane jersey may be suitable as moisture wicking fabric in the booster pad. In some embodiments, the cotton/elastane jersey is a knit comprising a blend of cotton and elastane, such as 80% cotton/20% elastane, 85% cotton/15% elastane, 90% cotton/10% elastane, etc. In some embodiments, the elastane is biobased elastane, being wholly or in part derived from a natural source such as a plant source. Preferably the moisture wicking fabric is a recycled/biodegradable version of the aforementioned materials.

One or more components of the pant undergarment of the invention may be air permeable and/or breathable. A preferred pant undergarment of the invention is hand and/or machine washable. A preferred pant undergarment of the invention has antimicrobial and/or odour minimising properties. One or more components of the pant undergarment may comprise one or more odour elimination treatments such as one or more of Sciessent Lava XL and Agion. Furthermore, a preferred pant undergarment of the invention solves the problem of odours arising from bodily fluids as well as keeping the wearer's skin dry.

Preferably, the fluid wicking component comprises a fabric which is derived from a natural fibre or a synthetic fibre. Natural fibres are preferred. Desirably, the fabric of the fluid wicking component may be hydrophilic or may comprise a hydrophilic material. Such materials may aid in wicking away bodily fluid away from the wearer's skin. Desirably, the fabric of the fluid wicking component may comprise keratinous fibres or other moisture-wicking or which are pre-treated to enhance the moisture-absorbing capabilities thereof. Preferred keratinous fibres are stain resistant. Otherwise, is desired, the fibres may be treated to render them stain resistant, with for example, Scotchguard™ or Teflon™.

Preferably, the fabric of the fluid wicking component is in the form of a knitted or a woven fabric, preferably knitted. Preferably, the brushed fluid wicking component includes an antimicrobial material or itself comprises fibres having antimicrobial properties, for example, such as wool, preferably a soft wool such as Merino wool. It will be understood that an antimicrobial material is one that has antibacterial, antiviral, and/or antifungal properties. The antimicrobial property minimises, and more preferably eliminates, odour arising from the bodily fluid. Suitably antimicrobial materials include silver ions.

Desirably, the moisture wicking fabric is a brushed fabric, preferably a brushed polyester fabric or a brushed polyester composite fabric. Preferably, the moisture wicking fabric of the booster pad is the same as the moisture wicking fabric of the pant undergarment of the first aspect.

The invention further extends to a kit comprising:

(i) one or more moisture management pant undergarments for wicking bodily fluid away from a wearer's skin into a fluid trapping core component of the undergarment, each garment comprising a pant body having a waist portion, a front panel and a back panel connected by a pair of side wings, and a pair of leg openings having a crotch panel or region disposed therebetween, wherein at least a portion of the crotch panel is overlaid with a floating liner assembly fixedly attached to the pant body and adapted to accommodate the fluid trapping core component which traps bodily fluid wicked away from the wearer's skin, wherein at least one or more portions of the floating liner and the crotch panel can be physically separated from each other to expose the fluid trapping core component to aid drying;

(ii) one or more removeable moisture management booster pads, each comprising a fluid trapping core component and an external covering surrounding the core component, the covering comprising a moisture wicking fabric.

In a preferred kit, the moisture wicking fabric booster component is the same as the moisture wicking fabric of the pant undergarment of the invention. Desirably, the moisture wicking fabric of the booster pad is the same as the moisture wicking fabric of the pant undergarment of the first aspect. In a preferred kit, the moisture wicking fabric booster component and the moisture wicking fabric of the pant undergarment each comprise brushed polyester comprising a brushed or otherwise textured surface having fibers displaced from the fabric knit. Preferably, the moisture wicking fabric of the booster pad and the pant undergarment comprises a brushed polyester fabric or a brushed polyester composite fabric which when used together form a friction/non-slip arrangement between the components which is desirably to prevent the booster sliding around or slipping out of the nappy completely during movement.

In a preferred kit, the moisture wicking fabric booster component and the moisture wicking fabric of the pant undergarment each comprise a brushed wool, particularly brushed Merino wool, a brushed wicking polyester, a brushed wicking polypropylene, a brushed wicking nylon, a brushed wicking micromodal, a brushed wicking bamboo, or composites thereof. Suitably, in a preferred kit, the moisture wicking fabric booster component and the moisture wicking fabric of the pant undergarment are each a brushed polyester composite, preferably containing more than 50% polyester and less than 50% spandex. Desirably, in a preferred kit, the moisture wicking fabric booster component and the moisture wicking fabric of the pant undergarment are each a brushed polyester composite comprising about 87% polyester and about 13% spandex.

In embodiments where the underwear garment is provided in the form of a nappy in a foldable configuration for folding into a nappy or an incontinence brief or incontinence underwear, or a toilet-training garments, it will be understood that the undergarment may include features such an elastic waist or an adjustable waist e.g., via adjustable press studs, buttons, hook & loop tape, clasps, hook & eyes or combinations thereof. The adjustable waist may be provided by positioning of side wings on the back panel of the garment that can be folded onto and temporarily affixed to the front panel of the garment. This allows the undergarment to be folded and sized appropriately for the wear's waist size. Likewise, the undergarment may include an adjustable crotch or gusset region, e.g., via adjustable press studs, buttons, hook & loop tape, clasps, hook & eyes or combinations thereof. This is particularly useful for nappies for children as the size can be adjusted appropriately as the child grows.

PREFERRED EMBODIMENTS/EXAMPLES

The present invention is described with reference to the following examples. It is to be understood that the examples are illustrative of and not limiting to the invention described herein.

FIG. 1 shows a top down schematic of one example of the invention in the form of a fold up nappy or diaper (1) in a flat or unfolded configuration. The nappy (1) comprises a nappy body having a front panel (F) and back panel (B) as indicated generally by the arrows in the schematic. The general position of a crotch panel (C) is also indicated, the edges (101, only one shown) of which are elasticated for comfort and assistance in avoiding leakages. Each of the front panel (F) and back panel (B) has respective upper edges (103), (105) which in this embodiment is elasticated, again to improved comfort and fit during use.

Each of the front panel (F) and back panel (B) has pair of side wings, front left side wing (106) and front right side wing (106') and back left side wing (108) and back right side wing (108').

Inner surface of each of the back left side wing (108) and back right side wing (108') are provided with one component of a hook & loop tape fastener (110, 110') which are attachable to an opposing component of the hook & loop tape fastener (not shown) positioned on the outer face of the front panel (F), preferably across the edge (103) of the nappy (1).

The inner (body facing) surfaces of the nappy body thus described are lined with a polybrush fabric generally designated (P) in the schematic.

Nappy (1) has a floating liner (112) which is attached to the front panel (F) and back panel (B) at their respective upper edges (103), (105). A floating liner (112) is also further attached to the back panel (B) in the region of the where the back left side wing (108) and back right side wing (108') extend into the side edges (101, only one shown) of the crotch panel (C) that form leg openings when in the folded configuration. Long side edges (114, only one shown) of the floating liner (112) are elasticated but are not attached to the nappy body. This means the floating liner (L) is physically separable from the nappy body to provide a region of space (S) between the floating liner (L) and the nappy body, particularly the crotch panel (C) of the nappy body. The underside of the floating liner (L) is provided with a fluid trapping core component (not shown) which in this embodiment is stitched to the underside of the floating liner (L). While the fluid trapping core component is not shown in this embodiment of the floating liner, the fluid trapping core comprises (under the polybrush liner) three layers of a polyester blend terry microfibre fabric (in this case a 80% polyester/20% polyamide fabric), two inner layers of which have a rectangular shape and are positioned as indicated by the stitching (116) outline, and one larger dimensioned layer which sandwiches the two inner layers and have the same shape as the floating liner (L).

The inner (body facing) surfaces of the floating liner (L) is lined with a polybrush fabric generally designated (P') in the schematic.

Figure 2:
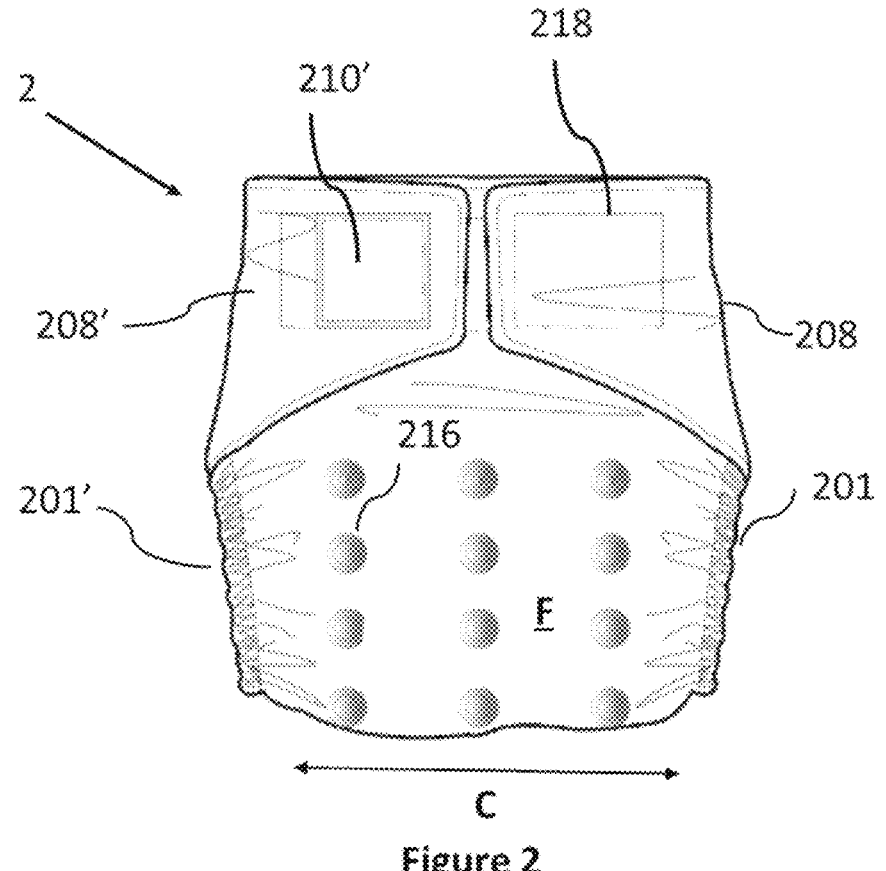
FIG. 2 illustrates a front on view of the fold up nappy of FIG. 1, which in this figure is shown in the folded configuration.

FIG. 2 shows a front view schematic of the nappy (2) in the folded configuration as adopted when worn. The front panel (F) is provided with press studs or buttons (216) in an array configuration and which enable resizing of the crotch panel and length of the nappy as desired.

Back left side wing (108) and back right side wing (108') are folded across the front of the nappy body and secured by one component of a hook & loop tape fastening (210, only one shown) to an opposing component of a hook & loop tape or fastener provided in the form of a band across the outer face of the front panel (F) as shown in outline (218).

FIG. 3 shows a back view schematic of the nappy (3) in the folded configuration as adopted when worn. The front panel (B), press studs or buttons (216) array and the hook & loop tape band (308) are clearly visible in this schematic.

FIG. 4 shows a front view schematic of the front panel (F) of nappy (4) in an unfolded configuration. The front panel (F) is provided with press studs or buttons (216) in an array configuration and which enable resizing of the crotch panel and length of the nappy as desired.

FIGS. 5a and 5b shows a top down schematic of one example of the invention in the form of a fold up nappy or diaper (5) in a flat or unfolded configuration. The nappy body front panel (F) and back panel (B) is visible, as are elasticated edges (501) that forms the leg openings when the nappy is folded for use. Floating liner (514) is indicated in this drawing in the position where it is physically contacting the nappy body, particularly in the crotch panel (C) area. A rectangular shaped outline is shown on the floating liner (514) which corresponds to the underside positioning of two layers of the absorbent microfibre fabric of the fluid trapping core component.

FIG. 5b shows a top down schematic of the fold up nappy or diaper (5) in a flat or unfolded configuration as before but having a booster pad (BP) positioned over the floating liner providing additional moisture absorbency to the crotch panel.

FIG. 6a illustrates an exploded view of the components of an example of a floating liner of the invention whereby upper outer layer (a) and lower outer layer (d) adopt the general shape of the floating liner. Layer (a) in this example is a polybrush moisture wicking fabric. In contrast, the remaining fabric layers (b), (c) and (d) are absorbent microfibre terry cloth fabric layers. Central layers (b) and (c) are rectangular shaped which adds additional absorbency to the central portions of the floating liner, while resulting in less bulk at the side edges of the liner which results in a more comfortable fit.

FIG. 6b illustrates an exploded view of the components of an example of a removeable moisture management booster pad for positioning over the lined crotch panel of a nappy, in which an external covering is formed from an upper outer layer (P'') and lower outer layer (P') which are a polybrush wicking fabric in this example, while inner layers (a'), (b'), (c'), (d'), (e') are all of absorbent microfibre terry cloth fabric layers. It will be understood that when the booster pad having polybrush surfaces are contacted with the polybrush outer fabric of the liner results in a friction or interference fit between the booster pad and the moisture wicking fabric lined parts of the underwear particularly the crotch panel. This stops/reduces slippage of the booster pad around in the nappy and moving out of the required position.

Figures 7A, 7B:
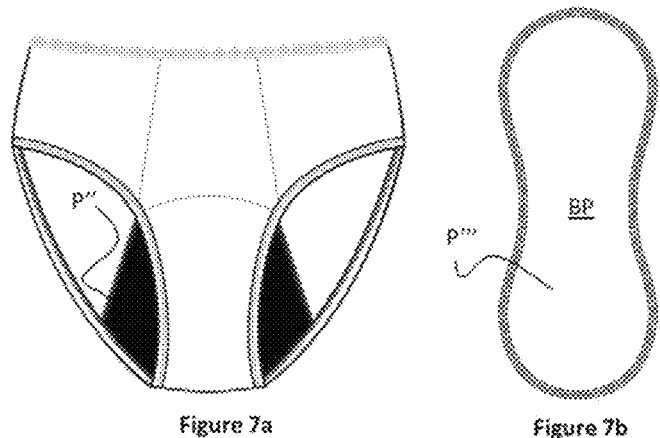
FIG. 7a illustrates a front on view of a pair of women's underwear having the floating liner assembly of the invention in the crotch panel region of the underwear.
FIG. 7b illustrates an example of a booster pad of the invention for use with a pair of women's underwear.

FIG. 7a illustrates a pair of women's underwear having the floating liner (P'') of the invention which comprises a wicking polybrush fabric in this example. FIG. 7b illustrates a booster pad for the pair of women's underwear of FIG. 7a, which has a curved/concave shaped side edges to improve the comfort experiences by the wearer in use.

Figure 7C:
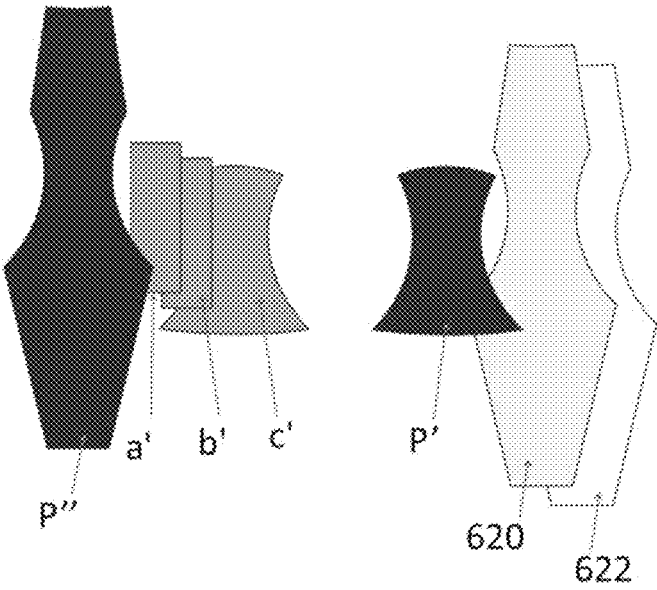
FIG. 7c illustrates an exploded view of the components of an example of a floating liner assembly of the invention for use in women's underwear.

FIG. 7c illustrates an exploded view of the components of an example of a floating liner for a pair of women's underwear whereby upper polybrush fabric outer layer (P'') adopts the general shape of the floating liner. Lower inner layer (c') is an absorbent microfibre terry cloth fabric adopting a crotch shaped panel, while remaining fabric layers (a'), and (b') are rectangular shaped absorbent microfibre terry cloth fabric layers add additional absorbency to the crotch areas in most need of additional absorbency. Furthermore, central layers (b) and (c) are rectangular shaped which adds additional absorbency to the central portions of the floating liner, while resulting in less bulk at the side edges of the liner which results in a more comfortable fit.

Figure 8A:
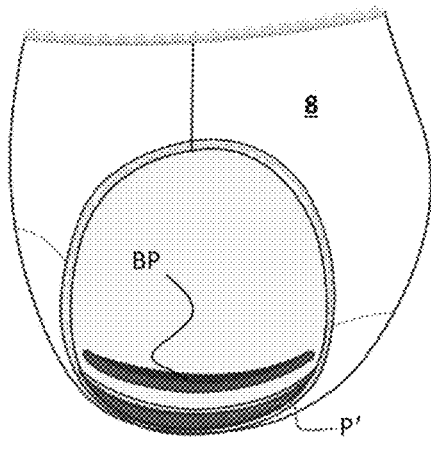
FIG. 8a illustrates a left side on view of a pair of women's underwear having the booster pad of the invention being positioned in the crotch panel gusset region of the underwear.
Figure 8B:
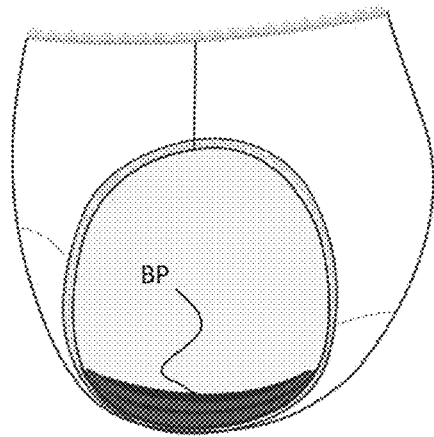
FIG. 8b illustrates a left side on view of a pair of women's underwear having the booster pad of the invention in position in the crotch panel region of the underwear.

FIGS. 8a and 8b shows a side view of the women's underwear of FIGS. 7a and 7b where a booster pad (BP) is included with a space between the booster pad and the polybrush (P') liner in this example. FIG. 8b shows the booster pad in the normal position contacting the floating liner whilst being worn.

FIG. 9a shows an exploded view of the fabric arrangement for a men's trunk style gusset layering, comprising a bamboo outer fabric (902), a waterproof layer (904) between the bamboo outer fabric (902) and a polybrush layer (906) forming the main construction of the trunk in the gusset/crotch area. FIG. 9a also shows the floating liner assembly comprising a first and second layer of microfibre terry (907, 909) and a polybrush inner layer (911) for contacting against the skin or a booster pad when included. FIG. 9b shows the full trunk outline with the main garment polybrush lining (906) shown, as well as the floating liner assembly provide with polybrush (911) facing the skin to be contacted when worn. FIG. 9c shows an exemplary booster pad for men's undergarments with additional volume capacity to one end of the pad.

Nappy Drying Time Test

A nappy according to the invention with a floating liner component is sewn up inner leg to outer leg to create an attached gusset. A further nappy according to the invention was left with the desired floating liner assembly in the floating configuration.

Each of the sample nappies were weighed while still dry before each nappy was fully saturated in water and both wrung out by hand three times to remove as much water as possible by hand. After this step, the wet nappies were weighed again before being hung out to dry. The nappy with the floating liner assembly was hung in a way that ensures airflow between outer crotch panel and floating liner assembly. Both are hung in same place, at the same point in time, under the same conditions.

After 12 and 24 hours drying time, the weight of the nappies is recorded. The results are provided below in Table 1 clearly demonstrating the nappy with the floating gusset has lost more water than the attached gusset nappy indicating the drying time benefit to the floating liner assembly feature on drying.

| | Floating Gusset | Attached Gusset |
| --- | --- | --- |
| Dry Pre-Testing | 148 g | 155 g |
| Wet, after wash and wrung | 300 g | 310 g |

23

-continued

| | Floating Gusset | Attached Gusset |
|---|---|---|
| After 12 hrs dry time | 239 g | 268 g |
| After 24 hrs dry time | 154 g | 181 g |

Brush Fabric Cleaning Tests

A mixture of crunchy peanut butter, toothpaste and Keens curry powder, plus a little water was mixed and used in place of faeces. One teaspoon of this mixture was added to a series of boosters for testing wherein the booster had different surface fabrics as identified in the table below.

A 10 cm scrape of the mixture was prepared with a serrated knife. The solid materials were scraped off each booster and the booster surface was inspected and the visual appearance was recorded below.

Approximately 8 ml of water was added to each resultant stain on the booster. Each booster was rubbed for 20 second by hand and the booster surface was inspected and the visual appearance was recorded below.

Each booster was then washed under a tap while rubbing for 30 seconds by hand, and the booster surface was inspected, and the visual appearance was recorded below.

Thereafter, each booster was machine washed for 15 minutes without detergent and the booster surface was inspected and the visual appearance was recorded below.

It is clear from the results of these tests that the polybrush fabric gave the best performance of all fabrics considered in terms of the faeces substitute tests. The faeces substitute can be scraped or wiped off easily, more so after gentle rubbing with all visible staining being removed after a 30 second hand wash and no staining or smells after a 15 minute machine wash.

| | Scrape | 20 Sec Rub | 30 Sec Hand Wash | 15 min machine wash |
|---|---|---|---|---|
| Polybrush Booster | Good - wipes off easily | Good - Solids rub off | Good - particles have washed off, no visible staining | Good - particles have washed off, no visible staining, smells clean |
| Grey Fleece Booster | Bad - engrained | Bad - engrained | Bad - many embedded particles remain, bad staining | OK, faint staining, smells of test solution, expect there are particles but less visible due to grey colour of fabric |
| White Fleece Booster | Bad - engrained | Bad - engrained | Bad - many embedded particles remain, bad staining | Bad - some embedded particles remain, bad staining, smells of test solution |
| Brushed Pile Bamboo Booster | Good - wipes off easily | Good - Solids rub off | OK - particles have washed off, bad staining | OK - particles have washed off but bad staining, smells of test solution |
| Jersey Knit Cotton Booster | Good - wipes off easily | Good - Solids rub off | OK - particles have washed off, bad staining | Bad - particles have washed off but really bad staining, smells of test solution |

The invention claimed is:

1. A launderable moisture management pant undergarment for wicking bodily fluid away from a wearer's skin, the undergarment comprising:

a pant body comprising leg openings having a crotch panel disposed therebetween, wherein at least a portion of the crotch panel is overlaid with a floating liner assembly partially fixedly attached to the pant body, the floating liner assembly comprises a fluid wicking fabric for contacting a wearer's skin in use and a fluid trapping core component permanently attached to the floating liner assembly which traps bodily fluid wicked away from the wearer's skin by the fluid wicking fabric, wherein the floating liner assembly has opposing short edges and opposing long edges, and the floating liner assembly is permanently attached to the pant body at both of the opposing short edges, and at least a portion of the floating liner assembly is detached from the pant body to allow physical separation of the portion of the floating liner assembly from the crotch panel to aid drying of the fluid trapping core component, wherein the long edges of the floating liner assembly proximate the leg openings of the pant body are elasticated such that the elasticated portions of the long edges float with respect to the pant body.

2. The pant undergarment of claim 1, wherein the floating liner assembly is attached at one end to a front panel of the pant body and attached at an opposing end to a back panel of the pant body.

3. The pant undergarment of claim 1, wherein one short edge of the floating liner assembly is attached a front panel of the pant body and an opposing short edge of the floating liner assembly is attached to the back panel of the pant body, or wherein one short edge of the floating liner assembly is attached to a front portion of the crotch panel of the pant body and the opposing short edge is attached to a back portion of the crotch panel of the pant body.

4. The pant undergarment of claim 1, wherein the fluid trapping core component is attached to an underside of the floating liner assembly, the underside being distal to a wearer's skin in use.

5. The pant undergarment of claim 1, wherein the fluid trapping core component is in a pocket provided in the floating liner assembly.

6. The pant undergarment of claim 1, wherein a second fluid trapping core component is attached to an upper side of the crotch panel, the upper side of the crotch panel being proximal to the wearer's skin in use.

7. The pant undergarment of claim 6, wherein the second fluid trapping core component is permanently attached to the upper side of the crotch panel or the second fluid trapping core component is removably attached to the crotch panel.

8. The pant undergarment of claim 7, wherein the second fluid trapping core component is in a pocket provided in the crotch panel.

9. The pant undergarment of claim 6, wherein the fluid trapping core component and/or the second fluid trapping core component comprises one or more layers of one or more layers of an absorbent, quick drying fabric.

10. The pant undergarment of claim 1, wherein the pant undergarment comprises a front panel and a back panel, and one or more of the front panel, the back panel, and the crotch panel comprise a moisture barrier component to prevent moisture leaking outside the pant during use.

11. The pant undergarment of claim 10, wherein the moisture barrier component comprises a moisture proof fabric, a moisture resistant fabric or a moisture repellent fabric.

12. The pant undergarment of claim 1, wherein the pant undergarment comprises a front panel and a back panel, and wherein one or more of the front panel, the back panel, and the crotch panel are lined on an inner surface with a moisture wicking fabric, the inner surface being proximal to the wearer's skin in use.

13. The pant undergarment of claim 1, wherein the moisture wicking fabric is cotton, a cotton blend, bamboo fleece, or a brushed fabric, or a composite or blend thereof.

14. The pant undergarment of claim 1, in the form of a launderable nappy, a launderable incontinence brief, launderable incontinence underwear, a launderable incontinence trunk, launderable incontinence pantyhose, launderable incontinence leggings, launderable incontinence gym shorts, a launderable toilet-training garment, launderable adaptive underwear, launderable tween/teen incontinence underwear, or launderable period management underwear.

15. The pant undergarment of claim 1, in a pull up conformation or a foldable configuration for folding into a wearable pant undergarment.

16. The pant undergarment of claim 15, wherein in the foldable configuration, each side of a back panel or a waist portion attached to the pant body comprises a fastening portion configured to reversibly attach to a front panel, which, when attached, forms a waist opening.

17. The pant undergarment of claim 16, wherein each fastening portion is in the form of a side wing.

18. The pant undergarment of claim 1, further comprising a removeable moisture management booster pad, wherein the booster pad comprises a fluid trapping booster core component sandwiched between two layers of a moisture wicking fabric booster component.

19. The pant undergarment according to claim 18, wherein the moisture wicking fabric booster component comprises a moisture wicking fabric selected from cotton, a cotton, bamboo fleece, or a brushed fabric having a brushed or otherwise textured surface having fibers displaced from the fabric knit, composites or blends thereof.

* * * * *